United States Patent [19]

Markham

[11] Patent Number: 4,931,059

[45] Date of Patent: Jun. 5, 1990

[54] NEEDLE/STYLET COMBINATION

[76] Inventor: Charles W. Markham, 667 Snug Island, Clearwater, Fla. 34630

[21] Appl. No.: 252,740

[22] Filed: Oct. 3, 1988

Related U.S. Application Data

[63] Continuation-in-part of Ser. No. 934,332, Nov. 24, 1986, Pat. No. 4,774,948.

[51] Int. Cl.$^5$ ............................................. A61B 17/34
[52] U.S. Cl. .................................................. 606/185
[58] Field of Search ...................... 128/329 R.751–754, 128/305, 303 R, 654; 604/164, 165, 178; 606/185

[56] References Cited

U.S. PATENT DOCUMENTS

| | | | |
|---|---|---|---|
| 2,541,246 | 2/1951 | Held | 128/305 |
| 4,592,356 | 6/1986 | Gutierrez | 128/339 |

*Primary Examiner*—Michael H. Thaler
*Attorney, Agent, or Firm*—A. W. Fisher, III

[57] ABSTRACT

A needle/stylet combination for use as a marking needle or retraction needle comprising a hollow needle including a barb slot formed in the distal portion thereof having a distal end configured to penetrate tissue, a stylet including a single resilient barb formed on the distal end thereof slidably disposed within the hollow needle, and a stylet retraction limiting structure formed on the stylet in space relationship relative to the distal end of the single resilient barb, the axial length of the spaced relationship thereof being greater than the axial length of the barb slot such that when the single resilient barb is positioned distally relative to the barb slot the hollow needle houses the single resilient barb and when the stylet member is retracted in a distal to proximal direction the proximal portion of the single resilient barb extends outwardly through the barb slot whereby the stylet retraction limiting structure engages the proximal end of the barb slot to retain the distal end of the single resilient barb within the hollow needle and as the stylet is advanced axially in the proximal to distal direction the single resilient barb re-enters the hollow needle.

7 Claims, 3 Drawing Sheets

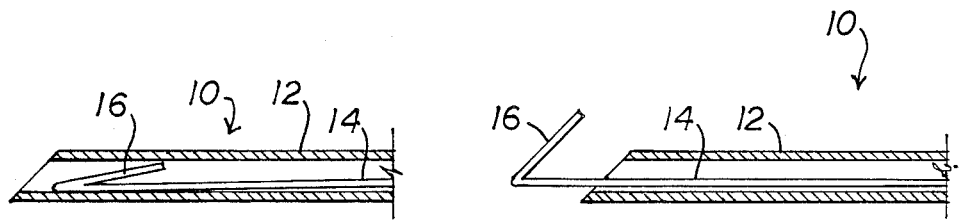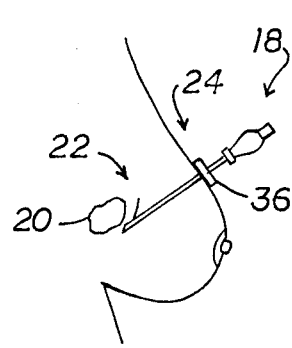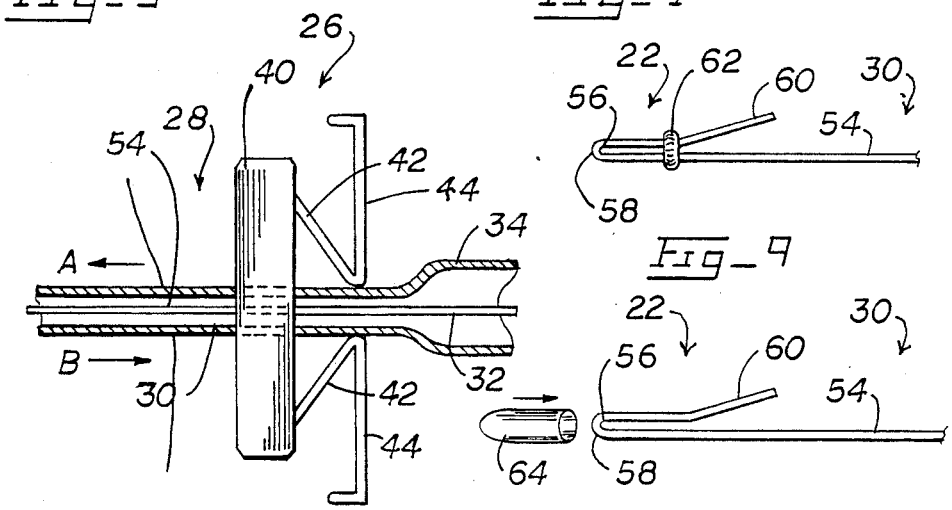

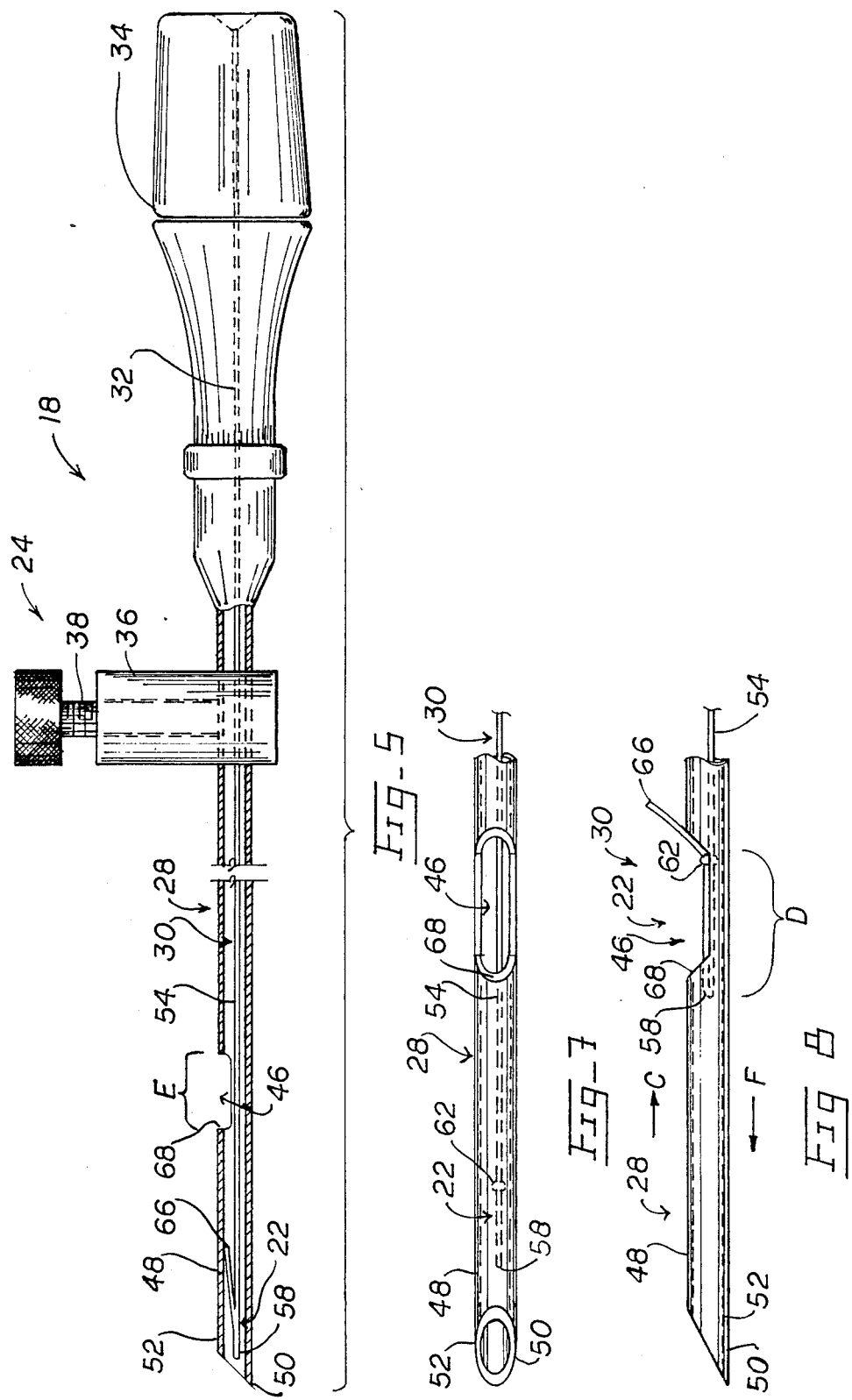

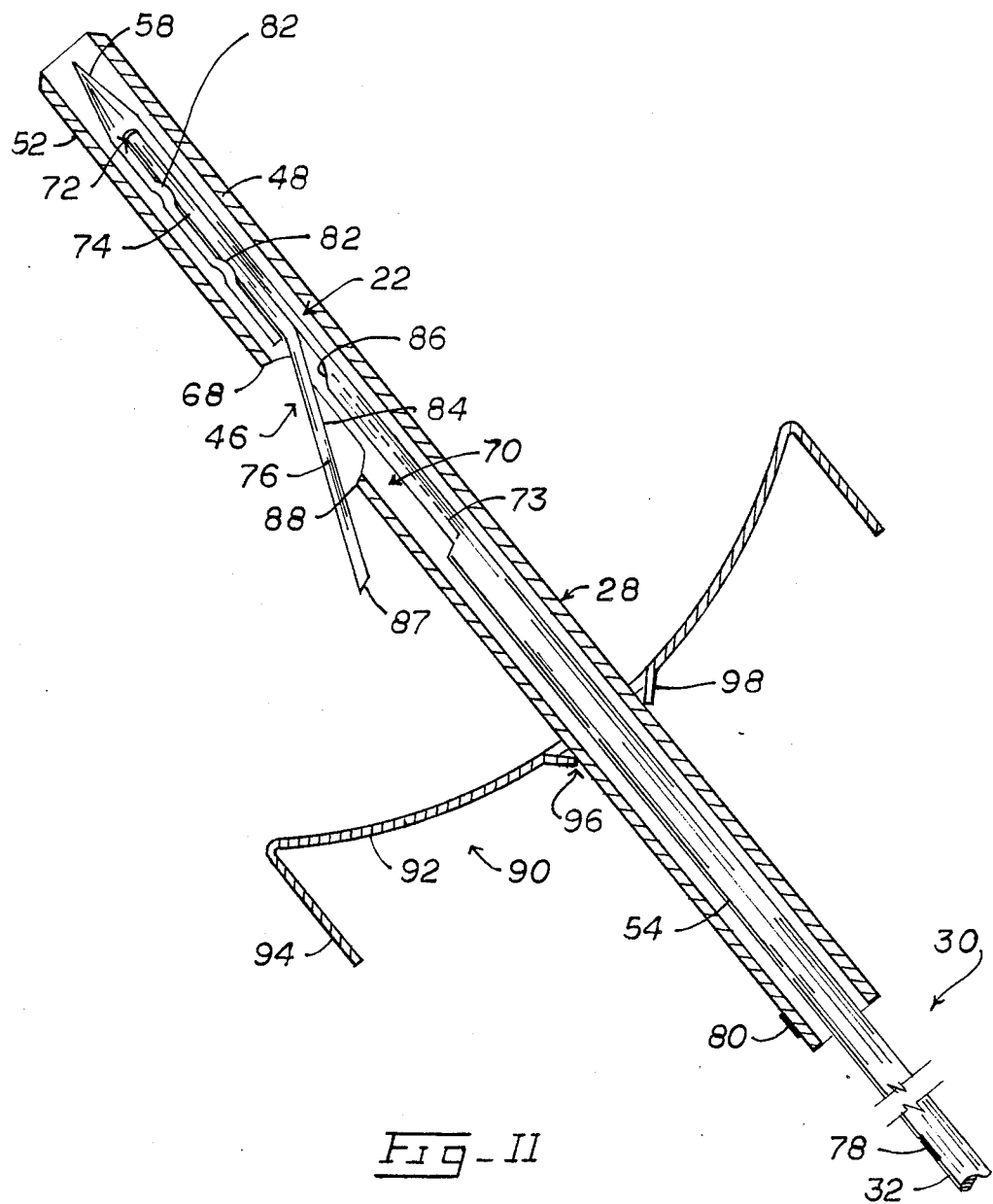
Fig-II

NEEDLE/STYLET COMBINATION

BACKGROUND OF THE INVENTION

1. Co-Pending Application

This application is a continuation-in-part application of Ser. No. 934,332 filed Nov. 27, 1986 now Pat. No. 4,774,948.

2. Field of the Invention

A marking and retraction needle used to mark the location of tumors prior to surgery.

3. Description of the Prior Art

Small tumors in the breast are often removed by surgical procedures. To avoid removal of excess tissue, the surgeon must be able to easily locate the tumor or area to be removed The prior art has developed a device known as a marking needle or localizer to mark the location of the tumor to be removed. Preparatory to surgery, the tip of the needle is placed adjacent the tumor to be removed.

Commonly a stylet comprising an elongate thin wire having a barb formed on the distal end thereof is used in combination with a hollow needle.

When the hollow needle is determined by X-ray to be properly positioned relative to the tumor, the stylet is axially advanced from the distal end of the hollow needle. The stylet is then retracted such that the barb engages and hooks tissue. The hollow needle is then removed leaving the stylet in place. The proximal end of the stylet extends out of the patient's body, remaining visible to serve as a marker that directs the surgeon to the tumor.

There are a number of problems with the marking needle just described.

U.S. Pat. No. 2.541.246 discloses a surgical instrument comprising a sheath having a slot formed therein, a rod disposed within the sheath, a cutting element independently pivoted to the rod and the sheath registering with the slot, and means for imparting movement to the rod relative to the sheath to thereby effect corresponding movement of the cutting element about the pivotal connections with the rod and sheath. More specifically, a flexible rod is disposed within the sheath. The rearward end of the flexible rod connected to a block is reciprocally disposed within the interior of the sheath in response to alternate forward and rearward pivotal movement of a handle. The forward extremity of rod is slotted or bifurcated. The cutting element registers with the slot in the rod and pivotally connected to the rod by a pin. The cutting element is also pivotally affixed to the sheath by a second pin.

U.S. Pat. No. 4.592.356 shows localizing needle having a pair of anchor-like barbs to firmly anchor the needle in skin or tissue so as to aid in location of lesions.

SUMMARY OF THE INVENTION

The present invention relates to an improved marking/ retraction needle.

The improved marking/retraction needle of the present invention includes a hollow needle having a stylet and barb disposed therein. The barb is employed to engage the tissue to anchor the position of the stylet/needle assembly or combination.

However, the barb may be disengaged from the tissue and the entire stylet may be non-surgically withdrawn and repositioned in the patient. The barb serves to stabilize the position of the needle relative to the tumor and when determined that the position is optimum the barb may be deployed for the needle.

Thus, all of the shortcomings of the marking/retraction needle now in widespread use are eliminated by the invention disclosed herein. Thus, the present invention is pioneering in nature representing as it does an important breakthrough which solves a number of longstanding but heretofore unfulfilled needs.

The advantage of the present invention derives primarily by a barb slot formed near the distal end of the hollow needle.

The provision of the barb slot enables the barb to extend therethrough and into tissue as desired without leaving the protective housing of the hollow needle.

Thus, the needle and stylet may both be held in place during the surgical removal of the tumor, the hollow needle serving to protect the stylet against inadvertent severing. Then, when the surgery has been completed and the specimen has been X-rayed, the stylet may be advanced forwardly. As the stylet is advanced forwardly, the resilient barb is constrained to disengage the tissue and to re-enter the hollow needle through the barb slot. The hollow needle and stylet are then easily removed from the patient.

The invention accordingly comprises the features of construction, combination of elements and arrangement or parts that will be exemplified in the construction hereinafter set forth, and the scope of the invention will be indicated in the claims.

BRIEF DESCRIPTION OF THE DRAWINGS

For a fuller understanding of the nature and object of the invention, reference should be had to the following detailed description taken in connection with the accompanying drawings in which:

FIG. 1 shows a marking needle of the prior art with a stylet and barb in a retracted position;

FIG. 2 shows the marking needle of FIG. 1 with the stylet and barb in an extended, tissue-engaging position;

FIG. 3 is a diagrammatic view of a breast having a tumor therein and the needle/stylet combination of the present invention;

FIG. 4 is a diagrammatic view of a breast having a tumor therein and an alternate embodiment of the needle/stylet combination of the present invention;

FIG. 5 is a detailed side view of the embodiment of the present invention of FIG. 3.

FIG. 6 is a partial detailed side view the embodiment of the present invention of FIG. 4.

FIG. 7 is a top view of a portion of the needle/stylet combination in the housed position;

FIG. 8 is a side view of a portion of the needle/stylet combination with the barb extending outwardly of the barb slot;

FIG. 9 is a detailed view of the distal portion of the stylet showing a stylet retraction limiting means;

FIG. 10 is a detailed view of the distal portion of the stylet showing an alternate embodiment of a stylet retraction limiting means;

FIG. 11 is a cross-sectional side view of still another alternate embodiment of the needle/stylet combination of the present invention.

Similar reference characters refer to similar parts throughout the several views of the drawings.

DETAILED DESCRIPTION OF THE PREFERRED EMBODIMENT

FIGS. 1 and 2 show a marking/retraction needle generally indicated as 10 representing the prior art. Specifically, the marking/retraction needle 10 comprises a hollow needle 12 having a stylet 14 operatively housed therein.

In operation, the marking/retraction needle 10 is inserted to mark the location of a tumor. Upon withdrawal of the hollow needle 12, the stylet 14 is physically held against withdrawal and thus emerges from the distal end of hollow needle 12 as shown in FIG. 2. The stylet 14 is then retracted slightly so that a barb 16 engages tissue thus anchoring the stylet 14 against further retraction. The stylet 14 and barb 16 must be surgically removed upon completion of the procedure.

FIGS. 3 and 4 diagrammatically show two embodiments of the present invention in operative position. The positions depicted are alternative and the various embodiments shown herein can be positioned in either of the two positions shown.

As shown in FIG. 3, the needle/stylet combination generally indicated as 18 is used as a marking needle since the position denotes the location of a tumor 20.

As shown in FIG. 4, the needle/stylet combination 18 is used as a retraction needle since the tumor 20 is positioned in the crotch of a barb generally indicated as 22.

In FIGS. 3 and 4, the needle/stylet combination 18 may include a needle holder generally indicated as 24 and 26 respectively positioned against the surface of the patient's skin to limit axial movement of the needle/stylet combination 18 as described more fully hereinafter.

As best shown in FIG. 5, the needle/stylet combination 18 comprises a hollow needle and stylet generally indicated as 28 and 30 respectively. As shown, the proximal end 32 of the stylet 30 may be disposed within a hub member 34.

As shown in FIGS. 3 and 5, the needle holder 24 comprises a disc or wafer 36 having a set screw 38 rotatably mounted thereon. When advanced, the set screw 38 engages the hollow needle 28 to lock the disc 36 in position relative to the hollow needle 28 to prevent any further advance of the hollow needle 28 into the patient's tissue (FIG. 3).

As shown in FIGS. 4 and 6, the needle holder 26 comprises an annular member 40 having a pair of resilient, diametrically opposed arms each indicated as 42 normally engaging the hollow needle 28 to prevent movement of the hollow needle 28 in the direction indicated by arrow A but allow movement of the hollow needle 28 in the direction indicated by arrow B. An element 44 is integral formed with each corresponding resilient arm 42. The physician may disengage the resilient arms 42 from the hollow needle 28 by depressing the gripper elements 44 to permit advancement of the hollow needle 28 in the direction indicated by arrow A. As shown in FIG. 4, the needle holder 26 is pressed against the surface of the patient's skin when in use.

As shown in FIGS. 5, 7 and 8, the hollow needle 28 includes a barb slot 46 formed in the distal portion 48 thereof and a penetration point 50 formed on the distal end 52 thereof.

FIGS. 9 and 10 show alternate embodiments of the stylet 30. In each embodiment the stylet 30 comprises an elongated stylet element 54 having the barb 22 formed in the distal end 56 thereof. The barb 22 comprises a first element or 180 degree return bend 58 and a second element 60 forming an acute angle relative to the first element 58. As shown in FIG. 8, retraction of the stylet 30 in the direction indicated by arrow C (distal to proximal direction) allows the second element 60 to project outwardly of the hollow needle 28 through the barb slot 46 when the barb 22 is aligned therewith.

Without means to limit the distal to proximal movement, the stylet 30 can be retracted too far by the physician permitting the distal end 56 thereof to pass through the barb slot 46.

FIG. 9 shows a stylet retraction limiting means comprising a weld 62 in spaced relationship relative to the distal end 56.

The distance D between the distal end 56 and the weld 62 (FIG. 8) is greater than the length E of barb slot 46 (FIG. 5) to prevent retraction of the distal end 56 through the barb slot 46.

FIG. 10 shows an alternate stylet retraction limiting means comprising a cap member 64 extending distally relative to the second element 60 formed on the stylet 30 in surrounding, capping relationship relative to first element 58 of the stylet 30.

It is important to observe the difference between the prior art as shown in FIGS. 1 and 2 and the present invention as shown in FIG. 8. The barbs 16 and 22 are operatively deployed and in engagement with tissue.

However, in FIG. 8, the barb 22 is still under the direct control of the physician whereas the barb 16 in FIG. 2 is no longer under such direct control, i.e., cannot be retracted into the hollow needle 12 by any means and removal from the patient must be accomplished surgically.

When the stylet 30 is axially advanced in the direction of arrow F (FIG. 8), the second element 60 being flexible, retracts into the barb slot 46 and becomes housed in the hollow needle 28 as shown in FIG. 7. It should be noted that the distance from the distal end 56 to the proximal end 66 of the barb 22 is less than the distance from the distal end 52 of the hollow needle 28 to the distal end 68 of the barb slot 46. Therefore, the barb 22 is fully housed within the hollow needle 28 as shown in FIGS. 5 and 7. Thus, both the hollow needle 26 and stylet 30 can be removed from the patient without surgery.

FIG. 11 shows still another alternate embodiment of the needle/stylet combination 18. Specifically, the hollow needle 28 includes a barb slot 46 formed through the distal portion 48 thereof.

The stylet 30 comprises an elongated stylet element 54 having a recess 70 formed in the distal portion thereof and a channel 72 formed in the distal end thereof to receive the barb 22. The inner portion of the recess 70 comprises a groove 73. The barb 22 comprises a first axially aligned element 74 and an inclined second element 76. The distal end 58 of the stylet 30 may comprise a penetration point while the proximal portion 32 thereof includes a first index 78 for cooperative alignment with a second index 80 formed on the hollow needle 28. As shown, the barb 22 is secured within the channel 72 by a plurality of crimps each indicated as 82. Alternate means of affixing or securing the barb 22 within the channel 72 may also be used. The stylet retraction limiting means comprises the lower surface 84 of the inclined second element 76 adjacent a pair of inclined notches 86 formed on the distal end of the recess 70, to selectively engage the proximal end 88 of the barb slot 46 when the stylet 30 is retracted relative to the hollow needle 28. The proximal end of the inclined second element 76 forms a cam surface 87.

The needle/stylet combination 18 further includes an alternate needle holder generally indicated as 90 comprising a flexible arcuate member 92 having a gripper 94 formed on the periphery thereof. A centrally disposed aperture 96 formed through the flexible arcuate member 92 is disposed in surrounding relationship relative to the hollow needle 28. A retainer element 98 formed on the flexible arcuate member 92 adjacent the centally disposed aperture 96 to normally engage the hollow needle 28. The flexible arcuate member 92 may be flexed to disengage the retainer element 98 from the hollow needle 28 to permit axial movement thereof similar to the needle holders 24 and 26. The flexible arcuate member 92 and retainer element 98 may comprise a composite of disimilar materials bonded together.

When the first index 78 is axially aligned relative to the second index 80, the second element 76 is axially aligned relative to the barb slot 46. Otherwise the operation of this alternate embodiment is similar to those previously discussed.

It will thus be seen that the objects set forth above, among those made apparent from the preceding description are efficiently attained and since certain changes may be made in the above construction without departing from the scope of the invention, it is intended that all matter contained in the above description or shown in the accompanying drawing shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,

What is claimed is:

1. A needle/stylet combination for use as a marking needle or retraction needle comprising a hollow needle including a barb slot formed in the distal portion thereof, a stylet including a single resilient barb affixed to the distal portion thereof, said stylet and single resilient barb normally disposed within said hollow needle, said single resilient barb including an inclined portion in spaced relationship relative to the distal end of said stylet, said stylet including a channel formed therein to receive the distal end of said single resilient barb and a recess to selectively receive said inclined portion, the axial length from distal end of said stylet to the distal end of said inclined portion being greater than the axial length of said barb slot such that when said single resilient barb is positioned distally relative to said barb slot, said hollow needle houses said single resilient barb and when said stylet is retracted in a distal to proximal direction said inclined portion of said single resilient barb extends outwardly through said barb slot whereby said inclined portion engages the proximal end of said barb slot to retain the distal end of said stylet within said hollow needle and as said stylet is advanced axially in the proximal to distal direction said inclined portion of said single resilient barb re-enters said hollow needle.

2. The needle/stylet combination of claim 1 further includes a needle holder to control proximal to distal movement of said hollow needle relative to the surface of a patient's skin when said hollow needle is operably positioned.

3. The needle/stylet combination of claim 2 wherein said needle holder comprises a flexible arcuate member having a gripper formed on the periphery thereof and a centrally disposed aperture formed therethrough disposed in relationship relative to said hollow needle, a retainer element formed on said flexible arcuate member adjacent said centrally disposed aperture to normally engage said hollow needle, said flexible arcuate member being flexed to disengage said retainer element from said hollow needle to permit axial movement thereof.

4. The needle/stylet combination of claim 1 further includes an index means to provide a visual indication of axial alignment of said inclined portion of said single resilient barb relative to said barb slot.

5. The needle/stylet combination of claim 4 wherein said index means comprises a first index formed on the proximal portion of said stylet and a second index formed on the proximal portion of said hollow needle.

6. The needle/stylet combination of claim 1 wherein the proximal end of said inclined portion comprises a cam surface.

7. The needle/stylet combination of claim 1 wherein said recess further includes an inclined notch formed on opposite sides thereof.

* * * * *